US008138354B2

(12) United States Patent
Foo et al.

(10) Patent No.: US 8,138,354 B2
(45) Date of Patent: Mar. 20, 2012

(54) N-SUBSTITUTED PYRROLIDONIUM IONIC LIQUIDS

(75) Inventors: Thomas Foo, Wilmington, DE (US); Mark Andrew Harmer, Landenberg, PA (US); Keith W. Hutchenson, Lincoln University, PA (US); Christopher P. Junk, Wilmington, DE (US); Berlyn R. Mellein, Wilmington, DE (US); Aaron Minter, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 49 days.

(21) Appl. No.: 12/328,057

(22) Filed: Dec. 4, 2008

(65) Prior Publication Data
US 2010/0145073 A1 Jun. 10, 2010

(51) Int. Cl.
C07D 207/12 (2006.01)
(52) U.S. Cl. ........................ 548/550; 252/364
(58) Field of Classification Search .............. 548/550
See application file for complete search history.

(56) References Cited

U.S. PATENT DOCUMENTS

| | | | |
|---|---|---|---|
| 2,913,496 A | 11/1959 | Cluff | |
| 4,820,672 A | 4/1989 | Mehta | |
| 5,608,105 A | 3/1997 | Fitzpatrick | |
| 5,859,263 A | 1/1999 | Ghorpade et al. | |
| 6,054,611 A | 4/2000 | Farone et al. | |
| 6,136,586 A | 10/2000 | Budowsky | |
| 6,579,343 B2 | 6/2003 | Brennecke | |
| 6,818,593 B2 | 11/2004 | Manzer | |
| 6,900,337 B2 | 5/2005 | Manzer | |
| 7,153,996 B2 | 12/2006 | Fagan | |
| 7,157,588 B2 | 1/2007 | Harmer | |
| 7,208,605 B2 | 4/2007 | Davis | |
| 7,314,962 B2 | 1/2008 | Harmer | |
| 7,544,813 B2 | 6/2009 | Harmer | |
| 7,625,941 B2 | 12/2009 | Harmer | |
| 7,744,838 B2 | 6/2010 | Davis | |
| 2004/0035293 A1 | 2/2004 | Davis | |
| 2004/0133058 A1 | 7/2004 | Arlt | |
| 2006/0197053 A1 | 9/2006 | Shiflett et al. | |
| 2006/0235230 A1* | 10/2006 | Harmer et al. | 548/402 |
| 2006/0276670 A1 | 12/2006 | Junk | |
| 2006/0276671 A1 | 12/2006 | Harmer | |
| 2007/0019708 A1* | 1/2007 | Shiflett et al. | 374/181 |
| 2008/0028777 A1 | 2/2008 | Boesmann | |
| 2010/0145074 A1 | 6/2010 | Foo | |
| 2010/0152465 A1 | 6/2010 | Davis | |

FOREIGN PATENT DOCUMENTS

| | | |
|---|---|---|
| WO | 03/048078 A2 | 6/2003 |
| WO | WO PCT/US09/66751 | 12/2009 |
| WO | 2010/065841 A1 | 6/2010 |
| WO | 2010/065873 A2 | 6/2010 |

OTHER PUBLICATIONS

Rantwijk et al. Chem. Rev. 2007, 107, 2757-2785.*
Horvath et al. Chem. Rev. 107, 2169-2173.*
Corma et al. Chem. Rev. 2007, 107, 2411-2502.*
Ranke et al. Chem. Rev. 2007, 107, 2183-2206.*
Horvath et al. Chem. Rev. 107, 2169-2173, 2007.*
U.S. Appl. No. 12/328,078, dated Dec. 4, 2008, Foo.
Yokozeki, Shiflett, Junk, Grieco and Foo, Physical and Chemical Absorptions of Carbon Dioxide in Room Temperature Ionic Liquids, J. Phys. Chem. B 2008, 112, 16654-16663, American Chemical Society, New York.
Marsh et al, Room Temperature Ionic Liquids and Their Mixtures—a Review, Fluid Phase Equilibria 2004, 219, 93-98; Elsevier, New York.
F. Zaragoza Dorwald, Side Reactions in Organic Synthesis: A Guide to Successful Synthesis Design, Weinheim: Wiley-VCH Verlag GmbH & Co., KGaA, 2005, Preface.
Letter dated Aug. 9, 2010 from Reggie Taylor, University of South Alabama, to P. Michael Walker.
International Search Report in PCT/US2009/066751, dated Feb. 5, 2010.
International Search Report and Written Opinion in PCT/US2009/066712, dated Feb. 10, 2010.
Cardoso et al, Synthesis, Characterization and Thermal and Dielectric Properties of Three Different Methacrylate Polymers with Zwitterionic Pendant Groups, J. Polymer Sci., Part B: Polymer Physics, 1997, vol. 35, pp. 479-488.
Lermit et al, Some Dichloroamine Derivatives, Journal of the Chem. Soc., 1947, pp. 530-533.
Koshar et al, Preparation of B-H-Perfluoro Alkanesulfionic Acids , J. Am. Chem. Soc., 1953, vol. 75, pp. 4595-4596.
Wasswescheid et al, Feedstock/Product Phase, Angew. Chem. Int. Ed., 2000, vol. 39, pp. 3772-3789.

* cited by examiner

*Primary Examiner* — Joseph Kosack
*Assistant Examiner* — Matthew P Coughlin

(57) ABSTRACT

This invention relates to compounds useful as ionic liquids that are based on an N-substituted pyrrolidinone and incorporate a pendant ammonium cation that is spaced from the pyrrolidone ring by a variable length linker, which compounds may be represented by the structure of the following Formula I:

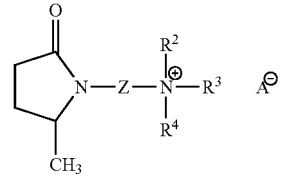

Formula I wherein:
(a) Z is —$(CH_2)_n$—, wherein n is an integer from 2 to 12;
(b) $R^2$, $R^3$ and $R^4$ are each independently H or a $C_1$ to $C_6$ straight-chain or branched alkyl group; and
(c) $A^-$ is levulinate, $[CF_3-O-CFHCF_2SO_3]^-$, $[CF_3CF_2OCFHCF_2SO_3]^-$, or $[CF_3CF_2CF_2OCFHCF_2SO_3]^-$.

8 Claims, No Drawings

N-SUBSTITUTED PYRROLIDONIUM IONIC LIQUIDS

TECHNICAL FIELD

This invention relates to N-substituted pyrrolidonium compounds that are useful as ionic liquids.

BACKGROUND

Ionic liquids are liquids composed of ions that are fluid at or below about 100° C. Ionic liquids exhibit negligible vapor pressure, and with increasing regulatory pressure to limit the use of traditional industrial solvents due to environmental considerations such as volatile emissions and aquifer and drinking water contamination, much research has been devoted to designing ionic liquids that could function as replacements for conventional solvents.

Ionic liquids typically consist of a salt of an organic cation such as the N-alkylpyridinium, 1,3-dialkylimidazolium, tetraalkylammonium, tetraalkylphosphonium or trialkylsulfonium cation. U.S. Pat. No. 7,157,588 describes, for example, ionic liquids based on N-substituted pyrrolidones, which have a pendant ammonium cation that is spaced from the pyrrolidone ring by a variable length linker. A need remains, however, for other ionic liquids that may be designed for use in selected applications, particularly those that may be prepared at least in part from renewable resources.

SUMMARY

This invention provides a compound represented by the structure of the following Formula I:

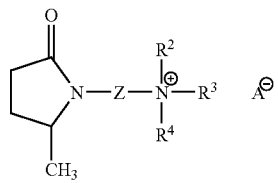

Formula I wherein:
(a) Z is —(CH$_2$)—, wherein n is an integer from 2 to 12;
(b) R$^2$, R$^3$ and R$^4$ are each independently H or a C$_1$ to C$_6$ straight-chain or branched alkyl group; and
(c) A$^-$ is levulinate, [CF$_3$—O—CFHCF$_2$SO$_3$]$^-$, [CF$_3$CF$_2$OCFHCF$_2$SO$_3$]$^-$, or [CF$_3$CF$_2$CF$_2$OCFHCF$_2$SO$_3$]$^-$.

DETAILED DESCRIPTION

This invention relates to compounds that are derived, in part, from N-substituted pyrrolidones. These compounds include an anion, and a cation in which there is a pendant ammonium cation spaced from a pyrrolidone ring by a variable length linker. This linker is denominated Z in the description of Formula I as set forth herein. These compounds are useful as ionic liquids, and can be used for example as a solvent, as a catalyst for various kinds of reactions (such as an alkylation reaction), and as an absorbent for various gases (such as CO$_2$). These compounds also have the advantage that the cationic portion, and some of the associated anions, may be readily prepared from levulinic acid, or levulinic acid derivatives, which may be obtained from the hydrolysis of inexpensive renewable biomass feedstocks.

In the description of the compositions hereof, the following definitional structure is provided for certain terminology as employed variously in the specification:

An "alkyl" group is a monovalent (i.e. having a valence of one) group having the general Formula C$_n$H$_{2n+1}$.

"Biomass" refers to any cellulosic or lignocellulosic material, and includes materials containing cellulose, and optionally further includes hemicellulose, lignin, starch, oligosaccharides and/or monosaccharides. Biomass may also include additional components such as proteins and/or lipids. Biomass suitable for use herein may be derived from a single source, or may be a mixture derived from more than one source. Such sources include without limitation bioenergy crops, agricultural residues, municipal solid waste, industrial solid waste, sludge from paper manufacture, yard waste, wood and forestry waste. Examples of biomass include without limitation corn grain, corn cobs, crop residues such as corn husks, corn stover, grasses, wheat, wheat straw, hay, rice straw, switchgrass, waste paper, sugar cane bagasse, sorghum, soy, residue from the milling of grain, trees, branches, roots, leaves, wood chips, sawdust, shrubs and bushes, vegetables, fruits, flowers and animal manure.

A "catalyst" is a substance that affects the rate of a reaction but not the reaction equilibrium, and emerges from the reaction chemically unchanged.

"Conversion" refers to the weight percent of a particular reactant that is converted in a reaction to product.

A "hydrocarbyl" group is a monovalent group containing only carbon and hydrogen.

An "ionic liquid" is an organic salts that is fluid at or below about 100° C.

A "levulinate" ion is an anion represented by the structure of the following formula:

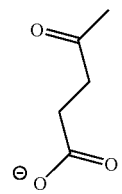

A "metal catalyst" is a catalyst that includes at least one metal, at least one Raney® metal, compounds thereof or combinations thereof. A supported metal catalyst is a supported catalyst in which the catalyst agent is a metal.

A "metal promoter" is a metallic compound that is added to a catalyst to enhance the physical or chemical function thereof in a reaction. A metal promoter can also be added to retard undesirable side reactions and/or affect the rate of the reaction.

A "promoter" is an element of the periodic table that is added to a catalyst to enhance the physical or chemical function thereof in a reaction. A promoter can also be added to retard undesirable side reactions and/or affect the rate of the reaction.

"Pyrrolidinone" is used synonymously with the term "pyrrolidone"; "pyrrolidin-2-one" is used synonymously with the term "2-pyrrolidone".

"Selectivity" refers to the weight percent of a particular reaction product in the total weight of the product of a reaction (including the weight of unreacted reactants).

This invention provides compounds represented by the structure of the following Formula 1:

Formula 1

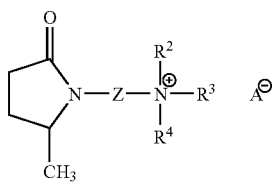

wherein (a) Z is —(CH$_2$)$_n$—, wherein n is an integer from 2 to 12; (b) R$^2$, R$^3$ and R$^4$ are each independently H or a C$_1$ to C$_6$ straight-chain or branched alkyl group; and (c) A$^-$ is levulinate, [CF$_3$—O—CFHCF$_2$SO$_3$]$^-$, [CF$_3$CF$_2$OCFHCF$_2$SO$_3$]$^-$ or [CF$_3$CF$_2$CF$_2$OCFHCF$_2$SO$_3$]$^-$.

In various embodiments, n in Z may be an integer from 2 to 6, and is frequently 2. In other embodiments, R$^2$, R$^3$ and R$^4$ may each independently be H, —CH$_3$, —CH$_2$CH$_3$ or —CH$_2$CH$_2$CH$_3$, and frequently R$^2$ and R$^4$ are —CH$_3$ and R$^3$ is —CH$_2$CH$_2$CH$_3$.

A compound hereof may be synthesized from a pyrrolidin-2-one as represented by the structure of the following Formula 2, wherein Z, R$^2$ and R$^3$ are as defined above.

Formula 2

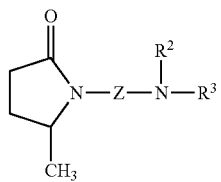

Synthesis of an N-hydrocarbyl pyrrolidin-2-one

The pyrrolidin-2-one may be synthesized by contacting levulinic acid, or an ester thereof, with a diamine of the Formula R$^2$R$^3$N—Z—NH$_2$ in the presence of hydrogen gas and a catalyst according to Reaction (I):

Reaction (I)

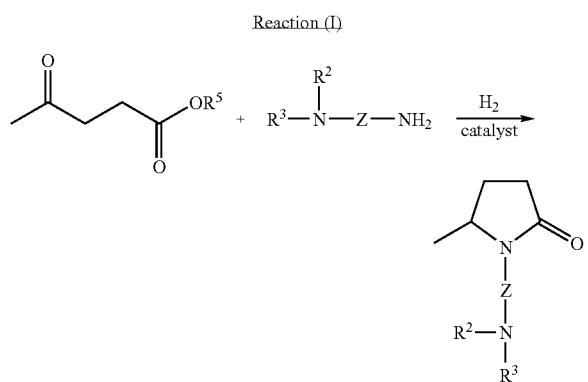

wherein Z, R$^2$ and R$^3$ are as defined above, and R$^5$ is H, —CH$_3$, —CH$_2$CH$_3$, or a C$_3$ to C$_8$ straight-chain or branched alkyl group. In another embodiment, the pyrrolidin-2-one may be synthesized by contacting a salt of levulinic acid, such as ammonium levulinate, with a diamine of the Formula R$^2$R$^3$N—Z—NH$_2$ in the presence of hydrogen gas and a catalyst. In various embodiments, in a diamine suitable for use herein, Z may be —(CH$_2$)$_n$— wherein n is an integer from 2 to 12, and R$^2$ and R$^3$ may each independently be H, —CH$_3$, —CH$_2$CH$_3$ or a C$_3$ to C$_6$ straight-chain or branched alkyl group.

The pyrrolidin-2-one formed in Reaction (I) can be synthesized according to methods and conditions as taught in or adapted from U.S. Pat. Nos. 6,818,593 or 6,900,337, each of which is by this reference incorporated in its entirety as a part hereof for all purposes. For the synthesis of a pyrrolidin-2-one according to Reaction (I), a molar ratio of diamine to levulinic acid, or a salt or ester thereof, at the start of the reaction may be about 0.01/1 to about 100/1, or about 0.3/1 to about 5/1. The temperature range for this reductive amination reaction may be from about 25° C. to about 300° C., or about 75° C. to about 200° C. The pressure may be in the range of from about 0.3 MPa to about 20.0 MPa, or from about 1.3 MPa to about 7.6 MPa. The reaction may be performed in a non-reacting solvent medium such as water or an alcohol, ether or pyrrolidone. Alternatively, an excess of diamine can also act as a reaction medium.

The principal component of a catalyst suitable for use in Reaction (I) may be selected from metals from the group consisting of palladium, ruthenium, rhenium, rhodium, iridium, platinum, nickel, cobalt, copper, iron, osmium; compounds thereof; and combinations thereof. A chemical promoter may augment the activity of the catalyst. The promoter may be incorporated into the catalyst during any step in the chemical processing of the catalyst constituent. Suitable promoters for this process include metals selected from tin, zinc, copper, gold, silver, and combinations thereof. The preferred metal promoter is tin. Other promoters that can be used are elements selected from Group 1 and Group 2 of the Periodic Table.

The catalyst may be supported or unsupported. A supported catalyst is one in which the active catalyst agent is deposited on a support material by a number of methods such as spraying, soaking or physical mixing, followed by drying, calcination and if necessary, activation through methods such as reduction or oxidation. Materials frequently used as a support are porous solids with high total surface areas (external and internal) that can provide high concentrations of active sites per unit weight of catalyst. A catalyst support may enhance the function of the catalyst agent.

The catalyst support useful herein can be any solid, inert substance including without limitation oxides such as silica, alumina and titania; barium sulfate; calcium carbonate; and carbons. The catalyst support can be in the form of powder, granules, pellets, or the like. A preferred support material is selected from the group consisting of carbon, alumina, silica, silica-alumina, silica-titania, titania, titania-alumina, barium sulfate, calcium carbonate, strontium carbonate, compounds thereof and combinations thereof. Supported metal catalysts can also have supporting materials made from one or more compounds. More preferred supports are carbon, titania and alumina. Further preferred supports are carbons with a surface area greater than 100 m$^2$/g. A further preferred support is carbon with a surface area greater than 200 m$^2$/g. Preferably, the carbon has an ash content that is less than 5% by weight of the catalyst support, where the ash content is the inorganic residue (expressed as a percentage of the original weight of the carbon) which remains after incineration of the carbon.

The preferred content of a metal catalyst in a supported catalyst is from about 0.1 wt % to about 20 wt % of the supported catalyst based on metal catalyst weight plus the support weight. A more preferred metal catalyst content range is from about 1 wt % to about 10 wt % of the supported catalyst. Combinations of metal catalyst and support may include any one of the metals referred to herein with any of the supports referred to herein. Preferred combinations of metal catalyst and support include palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica. Further preferred combinations of metal catalyst and support include palladium on carbon, palladium on alumina, palladium on titania, platinum on carbon, platinum on alumina, rhodium on carbon, rhodium on alumina, ruthenium on carbon and ruthenium on alumina.

A catalyst that is not supported on a catalyst support material is an unsupported catalyst. An unsupported catalyst may be platinum black or a Raney® (W.R. Grace & Co., Columbia Md.) catalyst. Raney® catalysts have a high surface area as a result of preparation by the selective leaching of an alloy containing the active metal(s) and a leachable metal (usually aluminum). Raney® catalysts have high activity due to the higher specific area and allow the use of lower temperatures in hydrogenation reactions. The active metals of Raney® catalysts include nickel, copper, cobalt, iron, rhodium, ruthenium, rhenium, osmium, iridium, platinum, palladium; compounds thereof; and combinations thereof. Promoter metals may also be added to the base Raney® metals to affect selectivity and/or activity of the Raney® catalyst. Promoter metals for Raney® catalysts may be selected from transition metals from Groups IIIA through VIIIA, IB and IIB of the Periodic Table of the Elements. Examples of promoter metals include chromium, molybdenum, platinum, rhodium, ruthenium, osmium and palladium, typically at about 2% by weight of the weight of the total metal.

Levulinic acid for use herein may be obtained from biomass. For the conversion of biomass to levulinic acid, biomass may be contacted with water and an acid catalyst in a train of one or more reactors, preferably under pressure at elevated temperature. This basic process is described, for example, in U.S. Pat. Nos. 5,608,105, 5,859,263, 6,054,611 and 7,153,996, each of which is by this reference incorporated in its entirety as a part hereof for all purposes. Generally, cellulose in the biomass is converted to levulinic acid and formate in one or more reactors. Levulinic acid produced from biomass may also be converted to levulinic acid esters for example as described in U.S. Pat. No. 7,153,996 through the reaction of levulinic acid with olefins.

Suitable diamines for use in Reaction (I) may, for example, be obtained commercially from suppliers such as Huntsman (Houston Tex.) or BASF (Mount Olive N.J.), or may be synthesized by methods such as those discussed in Eller and Henkes, *Diamines and Polyamines* [in Chapter 8 of *Ullmanns Encyclopedia of Industrial Chemistry* (2002), Wiley-VCH Verlag GmbH & Co.], or Chapter 22 in *Experimental Methods in Organic Chemistry*, $3^{rd}$ Edition [Moore, Dalrymple and Rodig (Eds.), (1982) Saunders College Publishing, NY].

The formation of a pyrrolidin-2-one may be carried out in batch, sequential batch (i.e. a series of batch reactors) or in continuous mode in equipment such as that discussed in Fogler, *Elementary Chemical Reaction Engineering*, $2^{nd}$ Edition [(1992), Prentice-Hall, Inc., N.J., USA]. A pyrrolidin-2-one synthesized according to Reaction (I) may be recovered, for example, by distillation, or by filtration to remove solid acid catalyst particles, if present.

Conversion of the N-hydrocarbyl pyrrolidin-2-one

A compound hereof may be synthesized by quaternizing the non-ring nitrogen of the pyrrolidin-2-one to obtain a quaternary ammonium compound as represented by the structure of the following Formula 3:

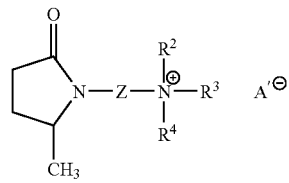

Formula 3 wherein Z, $R^2$, $R^3$ and $R^4$ are each as defined above, and $A'^-$ is selected from the group consisting of $Cl^-$, $Br^-$ and $I^-$.

To form a quaternary ammonium compound as described above, the pyrrolidin-2-one is contacted with an alkylating halide having the Formula $R^4$—A wherein $R^4$ is selected from the group consisting of a $C_1$ to $C_6$ straight-chain or branched alkyl group, and $A'^-$ is selected from the group consisting of $Cl^-$, $Br^-$ and $I^-$. The quaternization reaction may be carried out in an inert solvent such as acetonitrile, acetone or dichloromethane. The quaternization may be accomplished by refluxing of the reactants, optionally under an inert atmosphere. When the reactants are hygroscopic, it is preferable to carry out the quaternization reaction, and/or the anion exchange reaction described below, under conditions that exclude water and air. The alkylating halide is present in slight excess (e.g. about 5 wt % excess) at the start of the reaction. The reaction may be carried out at a temperature in the range of from about 10° C. to about 100° C.; or in the range of from about 30° C. to about 90° C.; or in the range of from about 60° C. to about 90° C. The time for the reaction is generally from about 1 minute to about 72 hours, or about 30 minutes to about 24 hours. Methods for performing quaternization reactions suitable for use for such purpose are further discussed in sources such as Organic Chemistry [Morrison and Boyd (ed.) $3^{rd}$ Edition (1973); Allyn and Bacon, Inc., Boston; Chapter 23.5, pages 752-753].

Anion Exchange

The quaternary ammonium compound thus formed is next contacted with $M^+A^-$, wherein M is selected from the group consisting of H, Li, K, Na, Ag, Mg, Ca, Ce, Ba, Rb and Sr, and $A^-$ is levulinate, $[CF_3-O-CFHCF_2SO_3]^-$, $[CF_3CF_2OCFHCF_2SO_3]^-$ or $[CF_3CF_2CF_2OCFHCF_2SO_3]^-$, to form a compound hereof according to the choice of anion desired. Prior to the exchange reaction, excess alkylating agent may be removed, for example, by evaporation. In addition, the quaternary ammonium compound may be washed with a solvent and dried prior to anion exchange.

The anion exchange reaction may be carried out by mixing the quaternary ammonium compound with $M^+A^-$, optionally under an inert atmosphere. The anion exchange reaction may be carried out at a temperature in the range of from about −20 C to about 100° C. for a time of about 1 second to about 72 hours. Solvents useful in the reaction should be inert to the reactants and products, and include, for example, methanol, ethanol, acetone and/or acetonitrile. Choice of the solvent or mixture thereof will facilitate separation of the compound containing the desired anion from the remainder of the reaction mixture. Additional techniques that may enhance the anion exchange reaction include as ultrasonication as discussed in WO 03/048078.

Fluoroalkyl sulfonate anions suitable for used in the anion exchange reaction may be synthesized from perfluorinated terminal olefins or perfluorinated vinyl ethers generally according to the methods discussed in Koshar et al [J. Am. Chem. Soc. (1953) 75:4595-4596], U.S. Ser. No. 06/276,670 and U.S. Ser. No. 06/276,671. In one embodiment, sulfite and bisulfite are used as a buffer in place of bisulfite and borax, and in another embodiment, the reaction is carried out in the absence of a radical initiator. The product of the anion exchange reaction may be recovered by a technique such as evaporation of the reaction solvent under reduced pressure, decantation and/or filtration to remove precipitated salts.

1,1,2,2-Tetrafluoroethanesulfonate, 1,1,2,3,3,3-hexafluoropropanesulfonate, 1,1,2-trifluoro-2-(trifluoromethoxy)ethanesulfonate, and 1,1,2-trifluoro-2-(pentafluoroethoxy)ethanesulfonate may be synthesized according to a modifications of Koshar in which

- a mixture of sulfite and bisulfite is used as the buffer, and freeze drying or spray drying isolates the crude 1,1,2,2-tetrafluoroethanesulfonate and 1,1,2,3,3,3-hexafluoropropanesulfonate products from the aqueous reaction mixture,
- acetone is used to extract the crude 1,1,2,2-tetrafluoroethanesulfonate and 1,1,2,3,3,3-hexafluoropropanesulfonate salts; and
- 1,1,2-trifluoro-2-(trifluoromethoxy)ethanesulfonate and 1,1,2-trifluoro-2-(pentafluoroethoxy)ethanesulfonate are crystallized from the reaction mixture by cooling.

Each of the formulae shown herein describes each and all of the separate, individual compounds that can be assembled in that formula by (1) selection from within the prescribed range for one of the variable radicals, substituents or numerical coefficients while all of the other variable radicals, substituents or numerical coefficients are held constant, and (2) performing in turn the same selection from within the prescribed range for each of the other variable radicals, substituents or numerical coefficients with the others being held constant. In addition to a selection made within the prescribed range for any of the variable radicals, substituents or numerical coefficients of only one of the members of the group described by the range, a plurality of compounds may be described by selecting more than one but less than all of the members of the whole group of radicals, substituents or numerical coefficients. When the selection made within the prescribed range for any of the variable radicals, substituents or numerical coefficients is a subgroup containing (i) only one of the members of the whole group described by the range, or (ii) more than one but less than all of the members of the whole group, the selected member(s) are selected by omitting those member(s) of the whole group that are not selected to form the subgroup. The compound, or plurality of compounds, may in such event be characterized by a definition of one or more of the variable radicals, substituents or numerical coefficients that refers to the whole group of the prescribed range for that variable but where the member(s) omitted to form the subgroup are absent from the whole group.

In various embodiments of this invention, an ionic liquid may be formed by selecting any of the individual cations described or disclosed herein, and by selecting to pair therewith any of the individual anions described or disclosed herein, and the ionic liquid(s) thus formed may be used for any of the purposes disclosed herein such as carbon dioxide absorption. Correspondingly, in yet other embodiments, a subgroup of ionic liquids may be formed by selecting a subgroup of any size of cations, taken from the total group of cations described and disclosed herein in all the various different combinations of the individual members of that total group, and pairing therewith a subgroup of any size of anions, taken from the total group of anions described and disclosed herein in all the various different combinations of the individual members of that total group. In forming an ionic liquid, or a subgroup of ionic liquids, by making selections as aforesaid, the ionic liquid or subgroup will be formed in the absence of the members of the group of cations and/or anions that are omitted from the total group thereof to make the selection, and, if desirable, the selection may thus be made in terms of the members of the total group that are omitted from use rather than the members of the group that are included for use.

The compounds hereof are useful as ionic liquids, and are in general fluid at or below a temperatures of about 100° C. The physical and chemical properties of an ionic liquid are influenced by the choice of cation. For example, increasing the chain length of one or more of the alkyl chains of the cation will affect properties such as the melting point, hydrophilicity/lipophilicity, density, viscosity, and salvation strength of the ionic liquid. Effects of the choice of cation and anion on the physical and chemical properties of an ionic liquid are further discussed in sources such as Wasserscheid and Keim [*Angew. Chem. Int. Ed.*, 39, 3772-3789 (2000)] and Sheldon [*Chem. Commun.*, 2399-2407 (2001)]. The compounds hereof may be utilized in one-phase systems or multiple-phase systems as a solvent, as a catalyst for various kinds of reactions (such as an alkylation reaction), and as an absorbent for various gases (such as $CO_2$).

Other related N-substituted pyrrolidonium compounds, and methods for using same for carbon dioxide absorption, are disclosed in the concurrently-filed, commonly-assigned applications listed as follows by attorney docket number and title, each of which is by this reference incorporated in its entirety as a part hereof for all purposes, to-wit:

(Functionalized N-Substituted Pyrrolidonium Ionic Liquids), now U.S. application Ser. No. 12/328,078;

(N-Substituted Pyrrolidonium Ionic Liquids with Expanded Linker), now U.S. Provisional Application No. 61/117,781; and (Carbon Dioxide Removal and Ionic Liquid Compounds Useful Therein), now U.S. Provisional Application No. 61/119,783.

EXAMPLES

Compounds provided by this invention, and the advantageous attributes and effects thereof, may be seen in a series of examples as described below. The embodiments of this invention on which the examples are based are representative only, and the selection of those embodiments to illustrate the invention does not indicate that materials, components and reactants, and/or conditions, protocols and regimes, not described in these examples are not suitable for practicing this invention, or that subject matter not described in these examples is excluded from the scope of the appended claims and equivalents thereof.

In the examples, the following abbreviations are used: nuclear magnetic resonance is abbreviated NMR; thermogravimetric analysis is abbreviated TGA; gas chromatography is abbreviated GC; gas chromatography-mass spectrometry is abbreviated GC-MS; thin layer chromatography is abbreviated TLC; centigrade is abbreviated C; mega Pascal is abbreviated MPa; gram is abbreviated "g"; milliliter is abbreviated "mL"; and hour is abbreviated "hr".

Materials.

The following materials were used in the examples. The commercial reagents and solvents acetonitrile (CAS Registry No. 75-05-8, 99.8% purity), 1-chloropropane (CAS Registry No. 540-54-5, 98% purity), dichloromethane (CAS Registry No. 75-09-2, 99.5% purity), diethyl ether (CAS Registry No. 60-29-7, 99% purity), ethyl levulinate (CAS Registry No. 539-88-8, 99% purity), ethyl acetate (CAS Registry No. 141-78-6, 99.8% purity), levulinic acid (CAS Registry No. 123-76-2, 98% purity), silver (I) oxide (CAS Registry No. 20667-12-3, 99% purity), and N,N-dimethylethylenediamine (CAS Registry No. 108-00-9, 98.0% purity, Fluka product) were obtained from Sigma-Aldrich Chemical Company (Milwaukee, Wis., USA), and were used as received without further purification. ESCAT® 142 catalyst (5 wt % palladium on activated carbon) was obtained from Engelhard (now BASF Catalysts, Iselin, N.J.).

Example 1 illustrates a method for the preparation of the 1-(2-(dimethylamino)ethyl)-5-methylpyrrolidin-2-one (MeDMAP) intermediate used in the subsequent preparation of various exemplary ionic liquids.

Example 1

Synthesis of 1-(2-(dimethylamino)ethyl)-5-methylpyrrolidin-2-one (MeDMAP)

1-(2-(dimethylamino)ethyl)-5-methylpyrrolidin-2-one (MeDMAP), $C_9H_{18}N_2O$, with a molecular weight of 170.25 g mol$^{-1}$ and structure as shown in Formula 4:

Formula 4

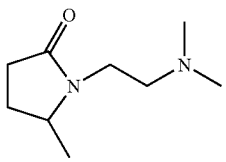

was prepared as follows via the cyclic reductive amination of ethyl levulinate with N,N-dimethylethylenediamine (and as further discussed in U.S. Pat. No. 7,157,588)

To a 600-mL Hastelloy® C-276 autoclave reactor (Parr Model 2302 HC) equipped with a gas entrainment turbine impellor and electrical heating mantle was added 150.0 g (1.04 mol) ethyl levulinate, 192.6 g (2.18 mol) N,N-dimethylethylenediamine, and 7.5 g ESCAT® 142 5% Pd/C catalyst. The reactor was purged first with nitrogen and then hydrogen, and then pressurized with 50 psig (0.4 MPa) hydrogen and stirred at 600 rpm while heating the reaction mixture to 150° C. On reaching this reaction temperature, the reactor was further pressurized to 1000 psig (7.0 MPa) with hydrogen and maintained at this pressure by adding additional hydrogen as required for the duration of the reaction.

After 6 hours at these conditions, the reactor was cooled and vented, and the liquid reaction mixture was recovered for product isolation. The crude mixture was filtered through a glass frit via aspirator vacuum to remove the catalyst followed by removal of byproduct ethanol and unreacted N,N-dimethylethylenediamine in vacuo. The remaining contents were fractionally distilled with a 20-cm Vigreaux column under high vacuum (~0.05 mmHg) to give 136.5 g water-white product at 85° C. in 77% isolated yield. Product purity was >99% as determined by GC/MS (HP-6890 equipped with MSD).

Example 2

Synthesis of 1-(N,N,N-dimethylpropylaminoethyl)-5-methylpyrrolidin-2-one levulinate ([MeDMPAP][Lev])

1-(N,N,N-dimethylpropylaminoethyl)-5-methyl pyrrolidone-2-one levulinate ([MeDMPAP] [Lev]), $C_{17}H_{32}N_2O_4$, with a molecular weight of 328.45 g mol$^{-1}$ and structure as shown in Formula 5, was prepared as follows:

Formula 5

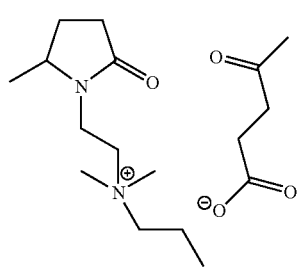

1-(2-(dimethylamino)ethyl)-5-methylpyrrolidin-2-one (MeDMAP), $C_9H_{18}N_2O$, with a molecular weight of 170.25 g mol$^{-1}$ and a purity of >99% by GC/MS, was used as prepared in Example 1. To a two-neck 100-mL round bottom flask equipped with a nitrogen-purged reflux condenser was added 18.30 g (0.108 moles) MeDMAP, 16.66 g (0.212 moles) 1-chloropropane, and 28.39 g acetonitrile as reaction solvent. The condenser was cooled by a recirculating bath filled with a 50 wt % mixture of water and propylene glycol maintained at approximately 16° C. The reaction mixture was heated to 85° C. under reflux and nitrogen purge with a temperature-controlled oil bath. This reaction temperature was maintained for 66 hrs, at which time the conversion of the MeDMP was about 78% by $^1$H NMR spectroscopy. The reaction mixture was then thermally quenched and dried under high vacuum (approximately 10$^{-6}$ torr) using a turbomolecular pump and heating the material to about 70-80° C. overnight.

The intermediate product of this reaction, 1-(N,N,N-dimethylpropylaminoethyl)-5-methyl pyrrolidone-2-one chloride ([MeDMPAP] [Cl]), $C_{12}H_{25}N_2OCl$, with a molecular weight of 248.79 g mol$^{-1}$, was then extracted with multiple diethyl ether extractions (approximately 300 mL in 30-50 mL increments) to remove starting materials, giving a final purity of about 97% [MeDMPAP] [Cl] by $^1$H NMR spectroscopy. This chloride salt was dissolved in dichloromethane, stirred with activated carbon overnight, poured through a column packed with neutral and acidic alumina, and then washed with methanol. The final purity of this chloride salt intermediate was approximately 99% by $^1$H NMR spectroscopy.

In a 500-mL Erlenmeyer flask, 5.031 g (0.0202 mol) of this [MeDMPAP] [Cl] intermediate was dissolved in approximately 150 mL of purified water. This solution was added to a slurry of 2.372 g (0.102 mol) silver(I) oxide and 2.596 g (0.0224 mol) levulinic acid in approximately 200 mL of purified water. After stirring overnight at room temperature, the reaction mixture was filtered through a fritted funnel containing Celite® to remove the silver chloride product and residual silver(I) oxide. Water was removed from the filtrate in vacuo with a rotary evaporator, then the product was twice dissolved in methanol, filtered through a fritted funnel containing Celite® to remove residual silver chloride and silver(I) oxide, and then evaporated in vacuo with a rotary evaporator to remove the methanol solvent. The product was then dried under high vacuum (approximately $10^{-5}$ torr) using a turbo-molecular pump and heating the material to about 70° C. for two days. The resulting [MeDMPAP] [Lev] product purity was 98.8% by $^1$H NMR spectroscopy.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

What is claimed is:

1. A compound represented by the structure of the following Formula I:

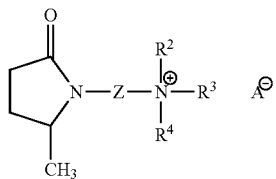

Formula I wherein
 (a) Z is —$(CH_2)_n$—, wherein n is an integer from 2 to 12;
 (b) $R^2$, $R^3$ and $R^4$ are each independently H or a $C_1$ to $C_6$ straight-chain or branched alkyl group; and
 (c) $A^-$ is levulinate.

2. A compound according to claim 1 wherein n is an integer from 2 to 6.

3. A compound according to claim 1 wherein n is 2.

4. A compound according to claim 1 wherein $R^2$, $R^3$ and $R^4$ are each independently H, —$CH_3$, —$CH_2CH_3$, or —$CH_2CH_2CH_3$.

5. A compound according to claim 1 wherein $R^2$ and $R^4$ are —$CH_3$.

6. A compound according to claim 1 wherein $R^3$ is —$CH_2CH_2CH_3$.

7. A compound according to claim 1 wherein n is an integer from 2 to 4, and $R^2$, $R^3$ and $R^4$ are each independently H, —$CH_3$, —$CH_2CH_3$, or —$CH_2CH_2CH_3$.

8. A compound according to claim 1 wherein n is an integer from 2 to 4, $R^2$ and $R^4$ are —$CH_3$, and $R^3$ is —$CH_2CH_2CH_3$.

* * * * *